US012622643B2

(12) United States Patent
Pelssers et al.

(10) Patent No.: US 12,622,643 B2
(45) Date of Patent: May 12, 2026

(54) FIXING OF A SENSOR TO A BODY PART FOR MEASUREMENT OF A BODY PARAMETER

(71) Applicant: KONINKLIJKE PHILIPS N.V., Eindhoven (NL)

(72) Inventors: Eduard Gerard Marie Pelssers, Panningen (NL); Hans Willem Van Kesteren, Eindhoven (NL); Jens Muehlsteff, Aachen (DE); Ralph Wilhelm Christianus Gemma Rosa Wijshoff, Munstergeleen (NL); Anthonius Petrus Gerardus Emanuels Janssen, Berghem (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 276 days.

(21) Appl. No.: 18/278,219

(22) PCT Filed: Mar. 2, 2022

(86) PCT No.: PCT/EP2022/055196
§ 371 (c)(1),
(2) Date: Aug. 22, 2023

(87) PCT Pub. No.: WO2022/184735
PCT Pub. Date: Sep. 9, 2022

(65) Prior Publication Data
US 2024/0138764 A1     May 2, 2024
Related U.S. Application Data

(60) Provisional application No. 63/157,228, filed on Mar. 5, 2021.

(51) Int. Cl.
*A61B 5/1455*     (2006.01)
*A61B 5/00*       (2006.01)

(52) U.S. Cl.
CPC ........ *A61B 5/6843* (2013.01); *A61B 5/14552* (2013.01); *A61B 5/6826* (2013.01)

(58) Field of Classification Search
CPC .............. A61B 5/1455; A61B 5/14552; A61B 5/6826; A61B 5/6843; A61B 2562/0233
See application file for complete search history.

(56) References Cited

U.S. PATENT DOCUMENTS 5,429,128 A * 7/1995 Cadell ................ A61B 5/14552
                                                    600/310
6,931,268 B1 * 8/2005 Kiani-Azarbayjany .....................
                                                    A61B 5/14552
                                                    600/322

(Continued)

FOREIGN PATENT DOCUMENTS

| JP | 2002159455 A | 6/2002 |
| JP | 2014171513 A | 9/2014 |
| WO | 2016097271 A2 | 6/2016 |

OTHER PUBLICATIONS

International Search Report Dated Jun. 21, 2022 For International Appln No. PCT/EP2022/055196 Filed Mar. 2, 2022.

(Continued)

*Primary Examiner* — Eric F Winakur

(57) ABSTRACT

A device is for measuring a body parameter for a subject. The device comprises a sensor for measuring the body parameter, a housing element for positioning the sensor on a body part of the subject and an actuator system within the housing element for applying a pressure to the body part. The actuator system comprises two states, a first state based on the actuator system applying a first pressure to a first area of the body part and a second state based on the actuator system applying a second pressure to a second area of the (Continued)

body part. The device also comprises a controller configured to apply the first and second states at different times.

15 Claims, 8 Drawing Sheets

(56) References Cited

U.S. PATENT DOCUMENTS

| | | | |
|---|---|---|---|
| 6,932,772 | B2 | 8/2005 | Kan |
| 7,613,488 | B1 * | 11/2009 | Maracas ............ A61B 5/14532 |
| | | | 600/322 |
| 9,839,362 | B2 | 12/2017 | Fournier |
| 10,314,496 | B2 | 6/2019 | Banet |
| 11,607,152 | B2 | 3/2023 | Moon |
| 2003/0236452 | A1 | 12/2003 | Melker |
| 2010/0324389 | A1 | 12/2010 | Moon |
| 2011/0152649 | A1 | 6/2011 | Scholl |
| 2013/0046159 | A1 | 2/2013 | Mccombie |
| 2017/0332966 | A1 | 11/2017 | Jacobs |
| 2018/0177413 | A1 | 6/2018 | Kwon |
| 2018/0338721 | A1 | 11/2018 | Wang |
| 2020/0408615 | A1 | 12/2020 | Scott |

OTHER PUBLICATIONS

Guo, D.G et al., "A long-term wearable vital signsmonitoring system using BSN", 11th Euromicro Conf. on digital system design architectures, methods and tools. pp. 825-830.

* cited by examiner

FIXING OF A SENSOR TO A BODY PART FOR MEASUREMENT OF A BODY PARAMETER

CROSS-REFERENCE TO PRIOR APPLICATIONS

This application is the U.S. National Phase application under 35 U.S.C. § 371 of International Application No. PCT/EP2022/055196, filed on Mar. 2, 2022, which claims the benefit of U.S. Provisional Application No. 63/157,228 filed on Mar. 5, 2021. These applications are hereby incorporated by reference herein.

FIELD OF THE INVENTION

The invention relates to a device for fixing to a body part of a subject. In particular, the invention relates to a device for measuring a body parameter of a subject whilst fixing itself to a body part of the subject.

BACKGROUND OF THE INVENTION

Pulse oximetry is a well known method to measure the saturation of hemoglobin with Oxygen. The associated sensor is a SpO2 sensor. Hemoglobin is a component of red blood cells and these cells are present in blood which flows through arteries, blood capillaries and veins. This method uses two light emitting diodes (LEDs) of different wavelengths and the light transmission is measured by a photodetector. From the pulsatile part of the transmitted light, a heart rate and a ratio between hemoglobin with bound Oxygen and without bound Oxygen can be determined. Ideally, the measured saturation of oxygen reflects the arterial Oxygen saturation.

The two LEDs and photodetector are integrated into a housing. These LEDs and optical detector are wired and these wires are collected into one cable. The cable is a shielded cable and may even consist of additional shields, for instance, around the wires to the detector and one around the wires to the LEDs. The other end of the cable is terminated by a connector that can be coupled to a patient monitoring instrument (Patient Monitor). The Patient Monitor supplies a voltage to both LEDs and reads the signal from the photodetector.

SpO2 sensors can be placed on different human body locations, such as the finger, nostril, forehead or ear. Fixing is carried out by exerting a pressure on the body location. There are reusable sensors that have a hollow elastic housing exerting continuous pressure on the body location such as a finger. Others employ a more rigid housing with a hinge and spring, again exerting a continuous pressure on a body location. In addition, disposable SpO2 sensors consist of a flexible material on which LEDs and detector are mounted. This flexible material is wrapped around the finger for fixing the sensor to the finger and can also exert a pressure on the finger. Besides providing fixing, pressure on the SpO2 sensor can also be used to suppress or reduce the contribution of pulsating venous blood and tissue fluid on the SpO2 signal.

SpO2 sensors for the finger have been available for many years. However, there is a compliance issue with users that remove the SpO2 sensor from the finger. The SpO2 sensor exerts a continuous pressure on the finger and consequently several users experience an uncomfortable feeling. Additionally, other sensors on other body locations (with sufficient blood perfusion for reliable measurement) fixed by exerting a continuous pressure can induce an uncomfortable feeling.

The effect of continuous pressure is a constant stimulation of nerves in the skin, which is translated to uncomfortable feeling by the brain. The blood flow is also partially restricted, generating further uncomfortable feelings. Complete blood flow restriction can even lead to local necrosis. This has been observed in forehead SpO2 sensors fixed with a stretched elastic band. It is often a challenge to find a suitable balance between sufficient pressure for accurate measurements and low enough pressure to be comfortable and guarantee sufficient blood flow even for users with blood perfusion issues.

Thus, there is a need for an improvement in comfort, and thus subject compliance, for devices which require (or benefit from) fixing of the device to a body part for the measurement of a body parameter (e.g. heart rate, blood pressure, oxygen saturation in blood, etc.).

SUMMARY OF THE INVENTION

The invention is defined by the claims.

According to examples in accordance with an aspect of the invention, there is provided a device for measuring a body parameter for a subject, the device comprising:
- a sensor for measuring the body parameter;
- a housing element for positioning the sensor on a body part of the subject;
- an actuator system within the housing element for applying a pressure to the body part, wherein the actuator system comprises two states:
  - a first state based on the actuator system applying a first pressure to a first area of the body part; and
  - a second state based on the actuator system applying a second pressure to a second area of the body part; and
- a controller configured to apply the first and second states at different times.

For example, devices used for measuring the saturation percentage of oxygen in blood (a SpO2 device) typically have compliance problems with subjects which find these devices uncomfortable and move or remove the devices. This is because SpO2 devices must be fixed to the body part which is being measured (e.g. finger, nose, forehead etc.) and this fixing causes a constant stimulation to nerves and a restriction of blood flow in the area to which the device is fixed. Over time, the constant stimulation and continuous restriction of blood flow cause discomfort to the subject.

The invention provides a device with an actuator system which allows the device to be fixed to the body part (at a single static position) whilst changing the area at which pressure is applied to the body part. The actuator system has two states, the first state during which pressure is applied to an area of the body part and the second state during which pressure is applied to a different area of the body part, thus limiting the time each area is stimulated and blood flow is restricted. The actuator system can also change the pressure amount between states. A controller is used to change the state of the actuator system based on pre-determined time periods (e.g. change state every 5 minutes, change state every 30 seconds etc.)

The device also has a sensor which measures a body parameter (e.g. heart pulse rate, respiration rate, photoplethysogram etc.) from the body part at which the device is fixed and a housing element which houses the sensor and the actuator system. The actuator system then fixes the device to the body part by producing a pressure between the housing element (and/or the sensor) and the body part which increases the friction between the device and the body part.

The actuator system may comprise at least two actuator elements, each actuator element being configured to change in volume or shape when the actuator element is stimulated, and wherein the controller is further configured to stimulate the actuator elements to define the state of the actuator system.

One way for the actuator system to fix the device to the body part is by using actuator elements. The actuator elements increase in volume or change in shape when they are stimulated and thus increase the pressure between the device and the body part.

For example, the device could be designed for measurements on a finger. The device may be placed around a finger (fully encircling the finger) and a first actuator element may then be stimulated.

The actuator elements for example fully encircle the finger. The actuation causes the actuator element to increase in volume or change in shape and thus cause a pressure between the housing element and the finger which fixates the device to the finger. After, for example, 5 minutes, the first actuator element may then be deactivated and a second actuator element may be stimulated.

When encircling the finger, the actuator elements may be spaced by only a few millimeters. The actuator system could have an even number of actuator elements which, as a whole, encircle the finger. The actuator system could then have a first number, n, of actuator elements on a top half of the system and an equal number, n, of actuator elements on a bottom half. Assuming four actuator elements on the top and bottom halves, in the first state of the actuator system, two of the actuator elements on the top half may be activated (i.e. be stimulated) and two of the actuator elements on the bottom half may also be activated (i.e. a first set of actuators). This causes four applied pressures from four directions which, in essence, clamp the device to the finger. When the actuator changes to the second state, the actuator elements will change to the ones which were not activated in the first state (i.e. a second set of actuators). In both states, the actuator system provides a fixing pressure between the finger and the device whilst changing between areas of the finger which have a pressure applied.

However, the actuator elements may instead be spaced along a line, for example the second actuator element could be at 10-50 mm distance along the length of the finger from the first actuator element, thus providing a pressure on a different area of the finger whilst maintaining the device fixed to the finger.

The actuator elements may be electro active polymers configured to expand in volume when a voltage is applied and the controller is further configured to apply a voltage to the electro active polymers.

Electro active polymers are convenient as they expand with an applied voltage. As the sensor will also require a voltage to power it, a shared power supply and cable arrangement may be used for both the sensor and the electro active polymers.

The actuator elements may instead be inflatable elements configured to expand when they are inflated.

The inflatable elements could be inflated by an external pressure pump. For example, pressure pumps which are typically used to inflate blood pressure cuffs could be used. The controller is then configured to actuate the pump.

The controller may be further configured to change the pressure applied to the body part of the subject by the actuator system.

The pressure required for different subjects may be different depending on, for example, subject's health, fat content, size of the body part etc. A particular pressure (at one or both states of the actuator system) may increase comfort from the device as well ensure more accurate measurements by the device.

The device may further comprise an accelerometer for determining the position of the subject and the controller is further configured to change the pressure applied to the body part of the subject by the actuator system based on the position of the subject.

The position of the subject may also affect the optimal pressure for any given subject. Thus, the accelerometer (e.g. 3D accelerometer) may give an indication of the position of the subject which can then be used to alter the pressure at one or both of the states of the actuator system.

The sensor may be a pulse oximeter which comprises an LED unit and a photodetector, wherein the photodetector is configured to obtain a signal relating to the saturation percentage of oxygen in blood.

A pulse oximeter indirectly monitors the oxygen saturation of a patient's blood (as opposed to measuring oxygen saturation directly through a blood sample). More specifically, it measures what percentage of hemoglobin, the protein in blood that carries oxygen, is loaded. Acceptable normal ranges for subjects without pulmonary pathology are from 95 to 99 percent.

The LED unit typically contains two LEDs which emit light at a different wavelength alternately. The photodetector then detects light from both LEDs after the light has been transmitted through a medium or reflected from the medium.

The LED unit may be placed at the extremity of a first actuator element and the photodetector may be placed at the extremity of a second actuator element.

The accuracy of pulse oximeters is typically dependent on the pressure applied between the components (LED unit and photodetector) and the body part. Thus, for example, an additional actuator system can provide a pressure between the sensor components and the body part and thereby increase accuracy. Additionally, by having the components of the sensor at the extremities of the actuator elements of the additional actuator system, the controller may control the pressure between said components (i.e. LED unit and photodetector) and the body part.

The controller may be further configured to control the actuator system to apply a pre-determined pressure to the body part, wherein the application of the pre-determined pressure to the body part reduces the venous contribution to the signal obtained by the photodetector.

The device may further comprise an adhesive layer at the interface between the housing element and the body part of the subject and wherein the actuator system is configured to apply a pressure between the sensor and the body part.

In some cases it may not be possible/realistic for the housing element of the device to encircle the body part and clamp it (e.g. forehead, torso etc.). In these cases, the housing element would benefit from an adhesive layer which enables the housing element to be fixed to the body part. The actuator system would then be used to apply a pressure to the sensor against the body part (e.g. reflective SpO2 sensor).

For example, the first state of the actuator system could ensure the sensor has a pressure against the body part. In order to reduce the discomfort from the pressure, the actuator system could change to a second state after a predetermined time period (e.g. 30 seconds to 5 minutes). The second state could then reduce the pressure applied to the area of body part or change the area to which pressure is applied.

The actuator system may comprise a rotating element with two or more protrusions and an elastic layer between the rotating element and the body part of the subject, wherein the controller is configured to rotate the rotating element when changing states.

The protrusions of the rotating element cause the elastic layer to bulge and thus provide a pressure on the body part from the elastic layer. The rotating element could then be rotated (e.g. 22.5 degrees, 45 degrees etc.,) when the state of the actuator system is changed, to change the area of the body part to which the pressure is applied, thus reducing discomfort for the subject.

If the elastic layer rotates with the rotating element, it may need to be fairly smooth (in the direction of the rotation) such that it does not harm the body part of the subject. Alternatively, the elastic layer may not move and the rotating element would change the position of the bulge on the elastic layer.

The device may further comprise a friction enhancing layer at the interface between the device and the body part of the subject.

A friction enhancing layer, i.e. a rough layer, at the interface of the device with the subject increases the friction on the body part, thus increasing the fixing of the device to the body part.

The device may further comprise a moisture trapping element at the interface between the device with the body part of the subject for reducing moisture build up at said interface. The moisture trapping element could also be disposably connected to the device so that it can be changed (e.g. for different subjects).

The invention also provides a method for measuring a body parameter for a subject, the method comprising:

applying a first pressure to a first area of a body part using an actuator system, wherein the actuator system is within a housing element and wherein the housing element is fixed to the body part;

applying a second pressure to a second area of the body part using the actuator system at a different time to the first pressure being applied to the first area of the body part; and measuring the body parameter with a sensor which is positioned on the body part by the housing element.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

Figure 1:
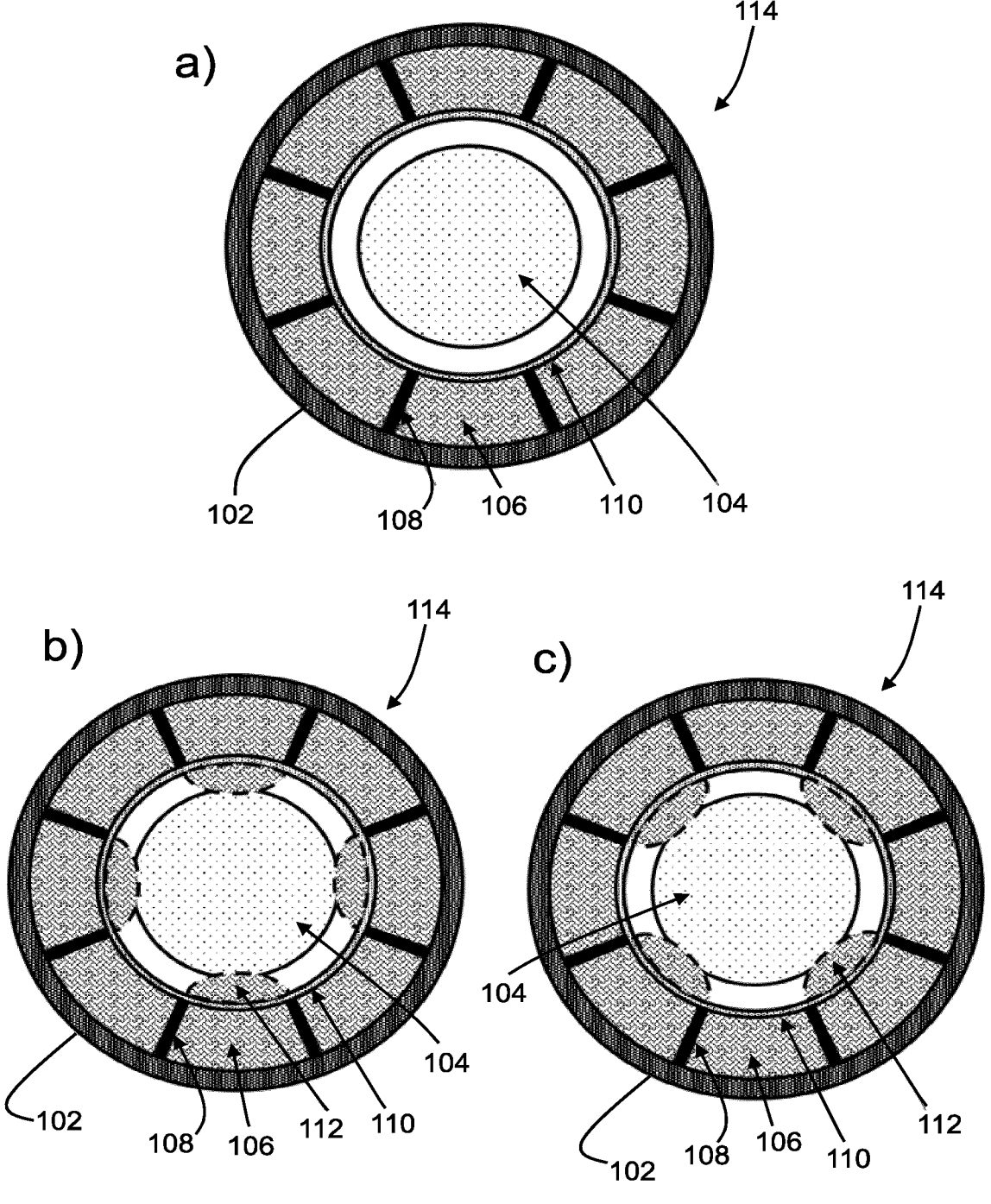
FIG. 1 shows an actuator device with electro active polymers as the actuator elements.

DETAILED DESCRIPTION OF THE
EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a device for measuring a body parameter of a subject. The device comprises a sensor for measuring the body parameter, a housing element for positioning the sensor on a body part of the subject and an actuator system within the housing element for applying a pressure to the body part. The actuator system comprises two states, a first state based on the actuator system applying a first pressure to a first area of the body part and a second state based on the actuator system applying a second pressure to a second area of the body part. The device also comprises a controller configured to apply the first and second states at different times.

Continuous pressure on a body location is circumvented by the actuator system by cyclically changing the body location used for fixing the housing, thereby locally and temporarily relieving the skin touch sensors, arteries and blood capillaries of a pressure.

FIG. 1 shows an actuator device 114 with an actuator system which comprises electro active polymers as actuator elements 106. Electro active polymer (EAP) actuator elements 106 translate an applied voltage directly to a volume expansion to apply an pressure for fixing the housing 102 to a body location 104. The grip of the actuator elements 106 may be enhanced by a friction enhancing layer 110 with sufficient roughness.

The actuator device 114 employs a number of EAP actuator elements 106 to apply a fixing which alternates in location, thereby minimizing impaired blood flow. A local electronic circuit may be used to convert a low supply voltage to a required higher voltage for driving the various EAP actuator elements 106, control the intermittent and alternate behavior of the EAP actuator elements 106 and, if required, interrupt the sensor measurement during the switching of the fixing locations on the body part 104. The switching of fixing locations changes the area of the body part to which pressure is being applied, from a first area to a second area of the body part 104, such that the first area has a relief from the pressure for a time period whilst the pressure is being applied to the second area, and vice versa.

The device can work for a variety of body parts 104. However, for the sake of the following examples, the body part 104 will be assumed to be a finger.

In FIG. 1*a*, a cross section is depicted of a housing 102 and eight EAP actuator elements 106. The other components, such as the sensor and the controller (i.e. electronic circuit), could be positioned at a different location in/on the housing 102 (hence not visible in the shown cross section). In the depicted cross section, two sets of four actuator elements 106 are shown. Both the cross section of the housing 102 as well of the finger 104 are displayed in a schematic fashion. The cross section of the finger 104 is highly schematically displayed as a circular cross section. However, the cross section of the housing 102 could be adapted to a shape with a better fit to the cross section of a finger 104, but this is not necessary for the functionality of the actuator device 114.

FIG. 1*b* shows a cross section of the device with the first set of actuator elements 106 activated (i.e. the actuator system is in a first state). FIG. 1*c* shows a cross section of the device with the second set of actuator elements 106 activated (i.e. the actuator system is in a second state). After placing the housing 102 over the finger 104 and subsequently powering the controller (e.g. by connecting the device to a patient monitor) the first set of the actuator elements 106 is activated and consequently the electro active polymer (of the activated actuator elements 106 in the first set) expands. The EAP actuator elements 106 are bordered by a rigid housing 102 and rigid separator elements 108. As such, they will bulge towards the finger 104 and in the process push a friction enhancing layer 110 (i.e. rough layer) with a defined roughness against the finger 104. The rough layer 110 separates the actuator elements 106 from the finger 104 and also has a roughness that aids in gripping the finger 104. The rough layer 110 also isolates the finger from the voltage that is applied to the actuator elements 106.

It should be noted that the use of the EAP actuator elements 106 is safe as they are operated on basis of an electrical field and the applied current for charging the electrodes of the EAP actuator elements 106 is small and perfectly safe in case of a breakage. The controller can be designed such that it only provides a small electrical current to the EAP actuators elements 106 (e.g. less than 5 mA).

After, for example, 30 seconds to 5 minutes, the second set of actuator elements 106 is actuated and the first set is then deactivated. After another 30 seconds to 5 minutes a similar process is initiated by activating the first set and then deactivating the second set. By repeating these actions, the pressure is alternately positioned at different areas of the finger as shown by the expanded sections 112 in FIG. 1*b* and FIG. 1*c*. In this case, the actuator elements 106 are segmented and consequently the finger 104 is not pressurized over its complete circumference thereby minimizing blocking of blood flow in the finger.

Alternatively, each set of actuator elements 106 can consist of less or more actuator elements 106 than the depicted four. For instance, each set could include only two actuator elements 106. This may be relevant for different sized fingers (e.g. babies and children have relatively small fingers thus may benefit from fewer actuator elements 106). Moreover, each set of actuator elements 106 could be placed at a different position along the length of the housing (i.e. a different cross section). These variations may further optimize the design and comfort based on the same principle of local and temporal relief of pressure.

Additionally, multiple actuator devices 114 may be providing along the length of the housing 102 with the advantage of increasing the fixing area on the finger 104 and, at the same time, lowering the pressure on the finger 104 by lowering the actuation level of the actuator elements 106.

Figures 2, 3:
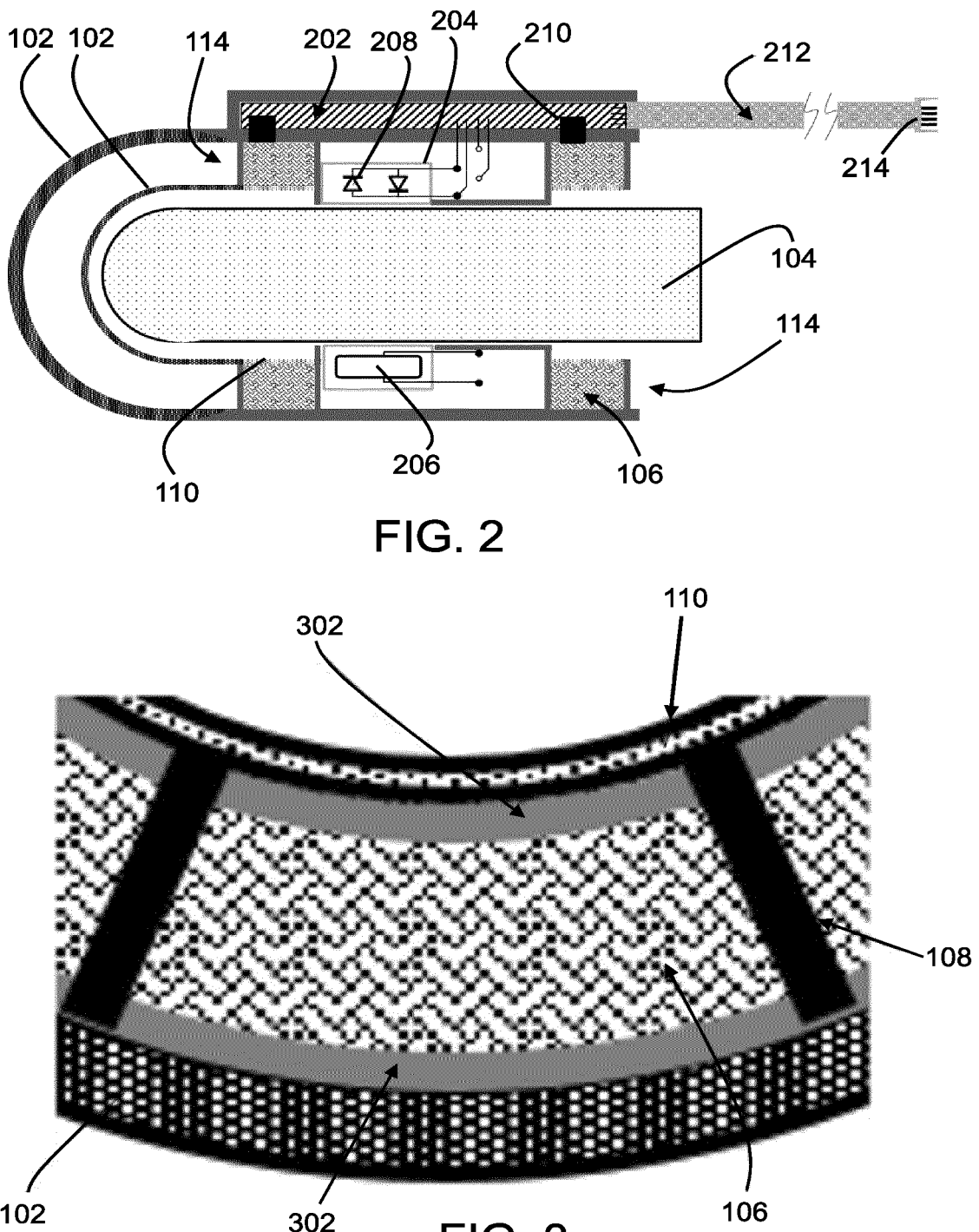
FIG. 2 shows a cross section along the length of the housing.
FIG. 3 shows an EAP actuator element with electrodes shown.

FIG. 2 shows a cross section along the length of the housing 102. In FIG. 2, the sensor is a pulse oximeter with an LED unit 204 (two LEDs 208) and a photodetector 206 for measuring the saturation of oxygen in the blood of the subject (i.e. SpO2 measurement). One LED 208 for example emit lights at a wavelength of 660 nm and the second LED 208 at a wavelength of 940 nm. The housing 102, controller 202 (an electronic circuit), cable 212 and connector 214 are also depicted. Two actuator devices 114 are depicted and they could, for example, be equivalent to the actuator device 114 discussed above.

The connector 214 (in this case, a male connector) has two pins that can be used for sensor identification. Identification can be achieved by measuring a resistor value or by reading data from a one wire device. A patient monitor can use this to identify the type of sensor connected. These pins also perform a dual function as explained below.

The pins are connected via the cable 212 to the electronic circuit 202. The advantage of using these two pins is that the delicate signal from the pulse oximeter is not coupled to the power for activating the actuator devices. The signal from the pulse oximeter is governed by a first set of pins feeding a pulsed signal to the LEDs 208 and a second set of pins that receive the signal from the photodetector 206 and the first and second set of pins could not be connected to the electronic circuit 202.

The electronic circuit 202 has two main functions. The first function is to return a resistor value (or one wire readout) to the patient monitor for identifying the type of sensor. The second function is to provide control of the actuator elements 106. In this case, the patient monitor supplies a voltage of, for example, 5 Volts via the pins and thereby provides power to the electronic circuit 202, and performs the identification. Subsequently the electronic circuit 202 increases the voltage to the desired voltage to drive the actuator elements 106, for instance by use of a voltage boost circuit, such as multiple voltage doublers. In the case of EAP actuator elements 106, this voltage is typically 200 Volts. However, for other actuator elements 106, 5 Volts may already be sufficient. Furthermore, the electronic circuit 202 has logic to alternately drive the two sets of actuator elements 106 in each one of the actuator devices 114.

The EAP actuator elements 106 are driven by an electrical field and, as such, they act like capacitors with low capacitance that require very little current.

A connection (point 210) between the electronic circuit 202 and the EAP actuator elements 106 can provide power to electrodes of the EAP actuator elements 106. The electrodes then provide the voltage to the electro active polymer material which expands.

FIG. 3 shows an EAP actuator element 106 with electrodes 302 shown. In a most basic arrangement, there may simply be a layer of EAP material sandwiched between electrodes. The EAP actuator elements 106 may however comprise a laminate of multiple electro active polymer layers sandwiched by electrodes 302. These electrodes 302 are then connected alternately to the voltage supply lines and a voltage of 200 Volts is applied for actuation of the electro active polymer layers. FIG. 3 is representation of a basic structure hence does not show the stacking of layers of electrodes 302 and electro active polymer layers. Only outer electrodes 302 are shown, which are connected to the electronic circuit 202, but other electrodes 302 may also be used.

Some sensors benefit from a pressure being applied between the sensor and the finger 104 (e.g. blood pressure sensors). Additionally, it may be advantageous for pulse oximetry, in particular to improve signal accuracy of the photodetector 206, to apply pressure on the finger 104 along the same axis as the light path from LED unit 204 to the photodetector 206.

Figure 4:
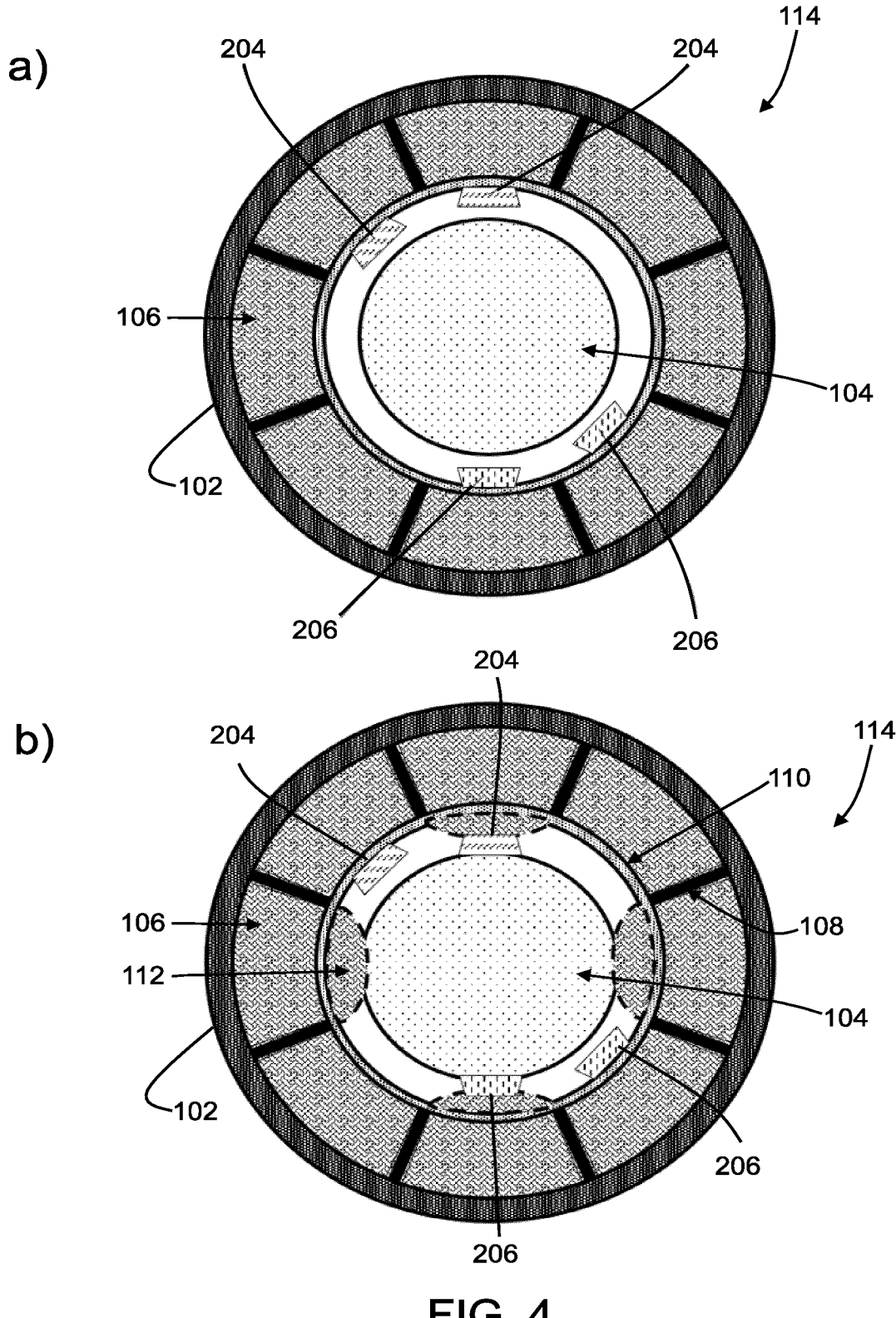
FIG. 4 shows an actuator device with an LED unit and a photodetector at the extremity of the actuator elements.

FIG. 4 shows an actuator device with an LED unit 204 and a photodetector 206 at the extremity of selected ones of the actuator elements 106. Preferably, for each "pressure direction" a separate LED unit 204 and photodetector 206 (e.g. photodiode) are incorporated. The various LED units 204 are activated in synchronism with the activation of their respective EAP actuator elements 106. In this case the LED unit 204 and photodetector 206 can each be located on top of an actuator element 106.

FIG. 4a shows the actuator device 114 when none of the actuator elements 106 is activated. FIG. 4b shows the actuator device 114 when a first (exemplary) set of actuator elements 106 is activated such that one diametrically opposing LED and photodetector pair is pressed against the body part.

For applications where an intermittent signal from the photodetector 206 is sufficient, a sensor with one LED unit 204 and one photodetector 206 can be combined with the EAP actuator elements 106. During an SpO2 measurement, the LED unit 204 and respective EAP actuator element 106 are activated while, between SpO2 measurements, the LED unit 204 is inactive when (one of) the other EAP actuator elements are activated. Additional actuator devices 114 could also be provided along the length of the housing 102 as explained above.

Figures 5, 6:
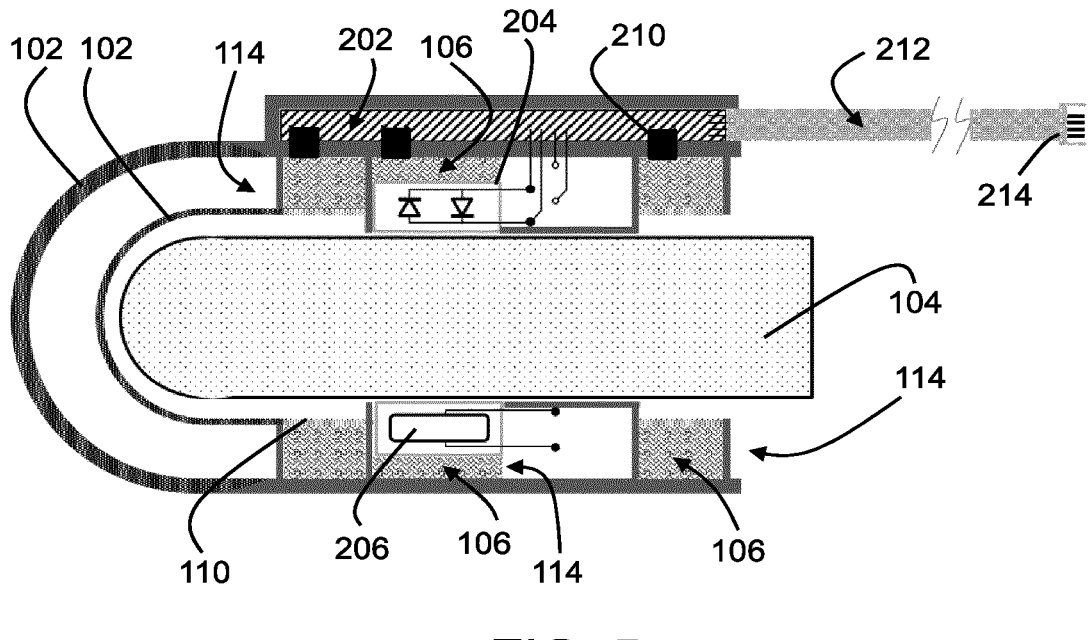
FIG. 5 shows the lateral cross section of a device with three actuator devices.
FIG. 6 shows the lateral cross section of a device with two actuator devices with inflatable actuator elements.

FIG. 5 shows a lateral cross section of a device with three actuator devices 114. Only one of the actuator devices 114 is used to press the LED unit 204 and the photodetector 206 to the finger 104.

In the case where an intermittent measurement is not sufficient, two LED units 204 and two photodetectors 206, mounted on associated actuator elements 106, may be used. In FIG. 5, one LED unit 204 and one photodetector 206 would be out of plane.

An arrangement of two (or more) circular actuator devices is also possible. For instance, in the case that the required pressure for fixing is relatively low and blood flow is only marginally limited, then all actuator elements 106 in one actuator device 114 can be activated all at the same time. When these actuator elements 106 are de-activated, the other actuator device 114 is activated resulting in a finger that is always fixed. In this case, the actuator elements 106 may also be replaced by one circular actuator element 106.

Other actuator elements 106, which are not based on electro active polymers, could also be used. For example, an inflatable element could be used.

FIG. 6 shows a lateral cross section of a device with two actuator devices 114 with inflatable actuator elements 106. The LEDs 208, photodetector 206, housing 102, cable 212 and connector 214 are also depicted for context. Two actuator devices 114 are shown. In this example, the actuator elements 106 are inflatable elements (e.g. balloons) that are inflated by a miniaturized pump 602 placed adjacent to the housing 102 which applies an pressure for fixing of the housing 102 to the finger 104 enhanced by a rough layer 110.

The electronic circuit 202 drives the pump 602. Additionally, a microfluidic circuit 604 with valves regulates which inflatable elements 106 are inflated and, if required, interrupts the SpO2 measurement during switching fixing locations.

Figure 7:
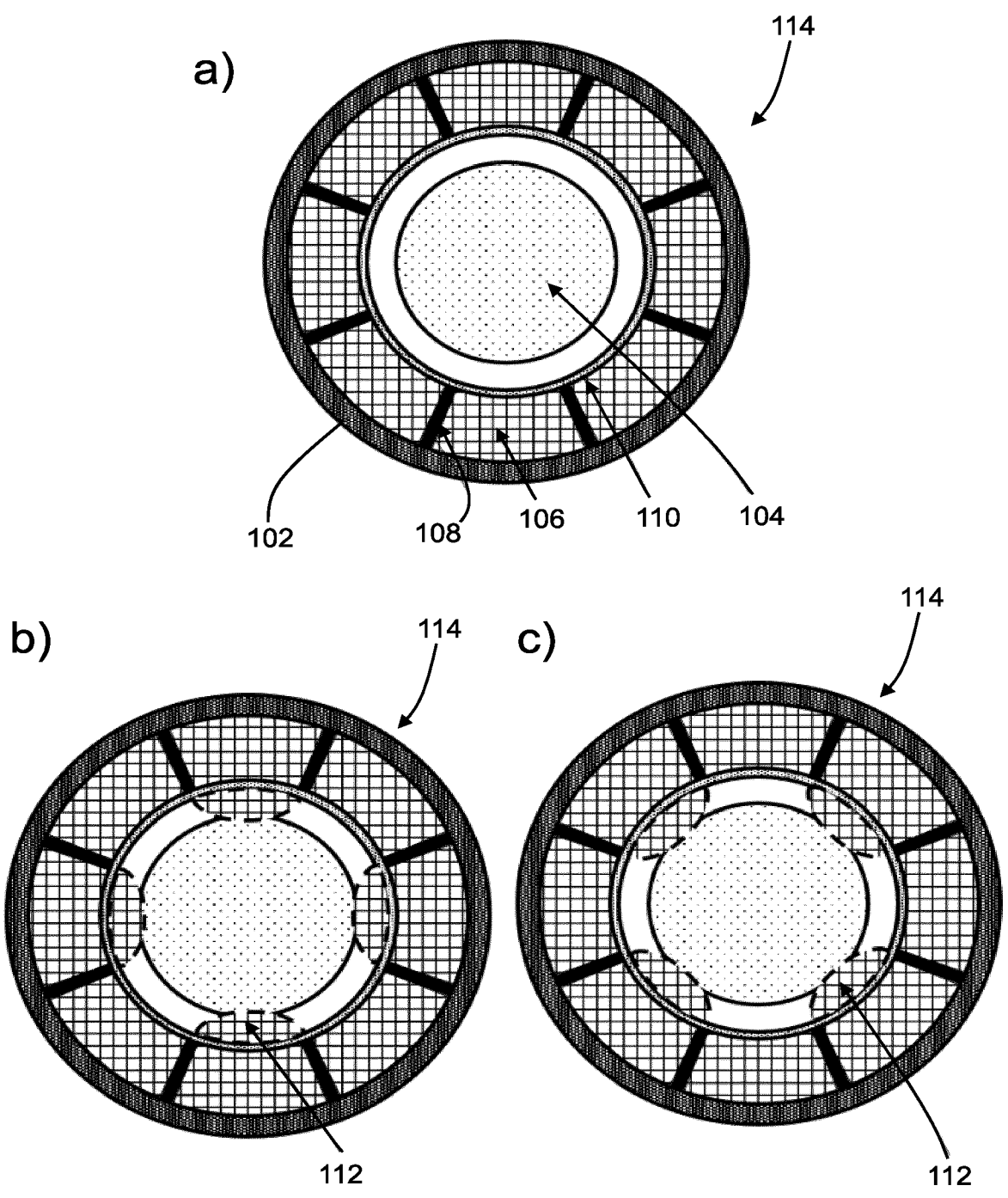
FIG. 7 shows an actuator device with eight inflatable elements.

FIG. 7 shows an actuator device 114 with eight inflatable elements 106. In FIG. 7a, a cross section is depicted of the actuator device 114 and the housing 104 when no inflatable elements 106 are actuated. The other components such as the LEDs 208, photodetectors 206, electronic circuit 202, microfluidic circuit 604 and pump 602 are positioned on a different cross section along the housing 102. In the depicted cross sections, two sets of four inflatable elements 106 are shown. FIG. 7b shows a first set of inflatable elements 106 activated (i.e. the actuator system is in a first state) and FIG. 7c shows a second set of inflatable elements 106 activated (i.e. the actuator system is in a second state). Both the cross section of the housing 102 as well of the finger 104 are again displayed in a schematic fashion After placing the housing over the finger and subsequently powering the electronic circuit 202 by, for example, connecting to a patient monitor, one set of the inflatable elements 106 begins expanding by activating the pump 602 and valves of the microfluidic circuit 604. Since each inflatable element 106 is bordered by a rigid housing 102 and rigid separator elements 108 it has to bulge towards the finger 104 and in the process pushes the rough layer 110 against the finger 104. Sections 112 in FIG. 7b and FIG. 7c show the bulging part of the inflatable elements 106 for a first set of inflatable elements 106 and a second set of inflatable elements 106 respectively.

The rough layer 110 separates the inflatable elements 106 from the finger 104 and also has a roughness that aids in gripping the finger 104. After 30 seconds to 5 minutes from when the first set of inflatable elements 106 is inflated (shown in FIG. 7b) the second set of inflatable elements 106 is expanded and immediately hereafter the first set is deflated (shown in FIG. 7c). After 30 seconds to 5 minutes a similar process is initiated by inflating the first set and immediately hereafter deflating the second set. By repeating these actions, the pressure is alternately positioned at different locations of the finger 104. In fact, the inflatable elements 106 are segmented and consequently the finger 104 is not pressurized over its complete circumference thereby minimizing the blocking of the blood flow in the finger 104. If desired, such an actuator device 114 can be repeated over the length of the housing 102 with the advantage of increasing the fixing area on the finger 104 and at the same time lowering the pressure onto the finger 104 by lowering the inflation of the inflatable elements 106.

There are various mini pumps 602 that can be deployed and can be driven by the electronic circuit 202 as previously described. In the case where a higher voltage would be beneficial for driving the pump 602, voltage boosting circuit such as voltage doubler circuits can be employed in the electronic circuit 202 as mentioned above. The electronic circuit 202 drives the pump 602 and valves in the microfluidic circuit 604 in such a manner that the two sets of inflatable elements 604 are alternately inflated.

The pump 602 can use air to inflate the inflatable elements 106. However, it could also use a hydro pneumatic fluid as air is compressible and hydro pneumatic fluids are practically incompressible. However, since an inflatable element 106 is a collapsible container, inflation is possible with either air or a hydro pneumatic fluid.

Figure 8:
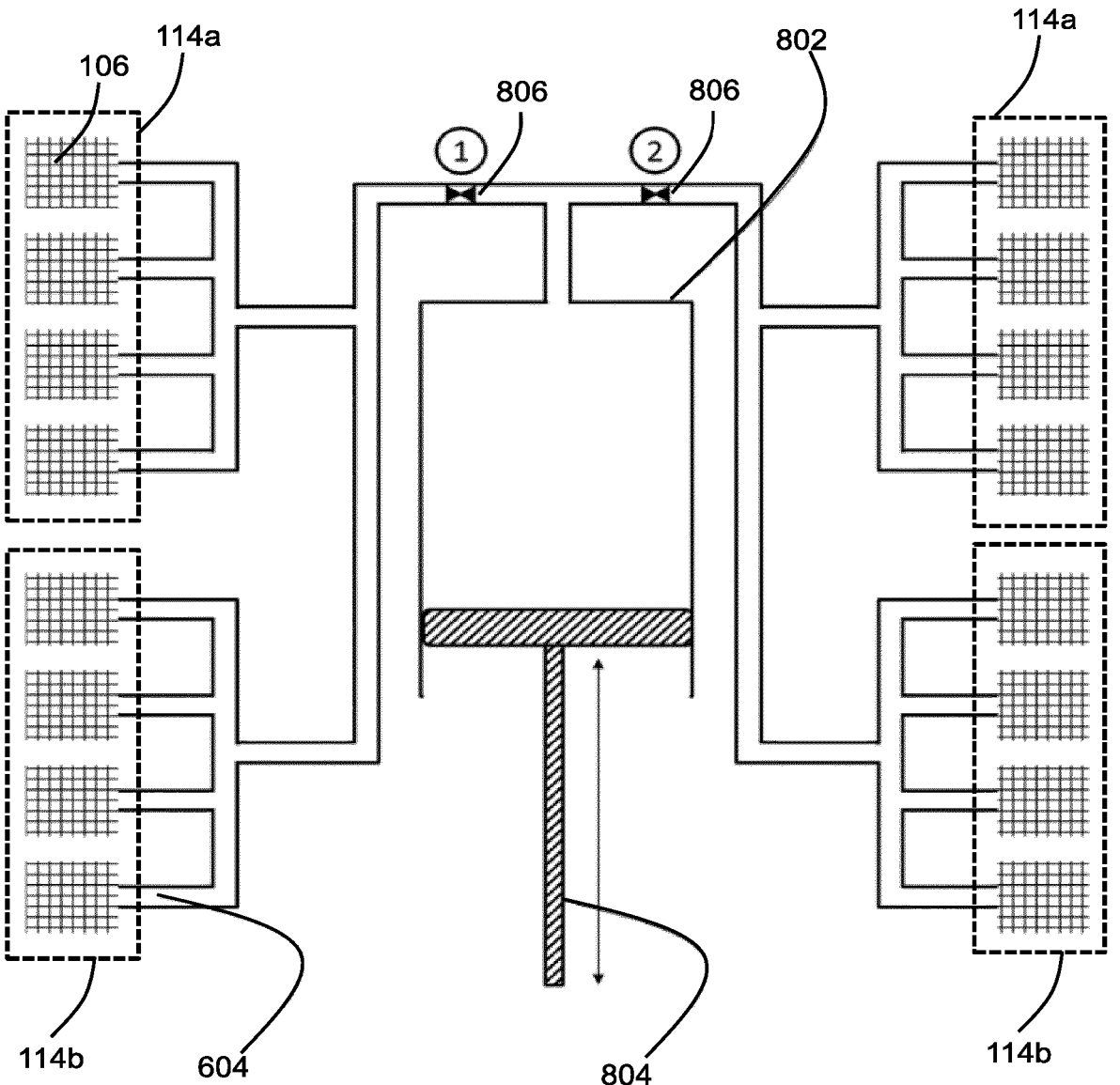
FIG. 8 shows a schematic representation of two actuator devices, each containing two sets of inflatable elements, and a microfluidic circuit with valves.

FIG. 8 shows a schematic representation of two actuator devices, 114a and 114b, each containing two sets of inflatable elements 106 and a microfluidic circuit 604 with valves 806. The microfluidic circuit 604 enables the inflation and deflation of the inflatable elements 106 induced by a mini-pump 602 made of a motor driving a plunger 804 into a syringe housing 802, thus changing the state of the actuator system. When the device is connected to a patient monitor, the electronic circuit 202 is activated. Subsequently, a first valve 806 (valve 1) is opened and the motor drives the plunger 804 into the syringe housing 802. Consequently, the inflatable elements 106 on the left side (i.e. a first set of inflatable elements 106 for the first actuator device 114*a* and a first set of inflatable elements 106 for the second actuator device 114*b*) are inflated, thereby gripping the finger 104.

After a certain time, typically between 30 seconds and 5 minutes, a second valve 806 (valve 2) is opened and the plunger 804 is driven further into the syringe housing 802, thereby inflating the inflatable elements 106 on the right side (i.e. a second set of inflatable elements 106 for the first actuator device 114*a* and a second set of inflatable elements 106 for the second actuator device 114*b*) as well. Immediately hereafter, valve 2 is closed and the plunger 804 is driven outwards and the inflatable elements 106 on the left side are deflated. The finger 104 is still fixed but now by the inflatable elements 106 on the right side. After 30 seconds to 5 minutes, the plunger 804 is driven inwards again, thereby inflating the inflatable elements 106 on the left side. Immediately hereafter, valve 1 is closed and valve 2 is opened. Hereafter the plunger 804 is driven outwards and the inflatable elements 106 are deflated on the right hand side. This is repeated in a cyclic manner. The microfluidic circuit 604, the mini pump 602, and/or the valves 806 are for example located on the PCB of the electronic circuit 202 (not drawn). There are various state-of-the-art mini pumps 602 (e.g. motor & syringe) that can be used.

For SpO2 measurements, it is advantageous to apply pressure on the finger 104 along the same axis as the light path from LEDs 208 to the photodetector 206. Preferably, for each "pressure direction" a separate LED unit 204 is incorporated. The various LED units 204 are activated in accordance with the activation of their respective inflatable elements 106. In this case the LED's 208 could be located on top of an inflatable element 106. Additionally, the photodetector 206 could also be placed on top of an inflatable element 106.

As explained above, for applications where an intermittent SpO2 measurement is sufficient, a sensor with one LED unit 204 and photodetector 206 can be combined with inflatable elements 106 along one direction. During an SpO2 measurement, the LED unit and respective inflatable element 106 is activated while in between SpO2 measurements the LED unit is inactive and (one of) the other inflatable elements 106 in the actuator system is activated.

Any other pumps 602 that employ a pressure to an inflatable element 106 (including ones using hydraulics) may be used instead of the depicted plunger 804 and syringe housing 802. These may be miniaturized MEMS pumps. Alternatively, the pressure pump typically used for inflating cuffs may be used (e.g. the pressure pump in a patient monitor). This would require an additional pressure line in the cable 212 and connector 214 to the patient monitor.

Figure 9:
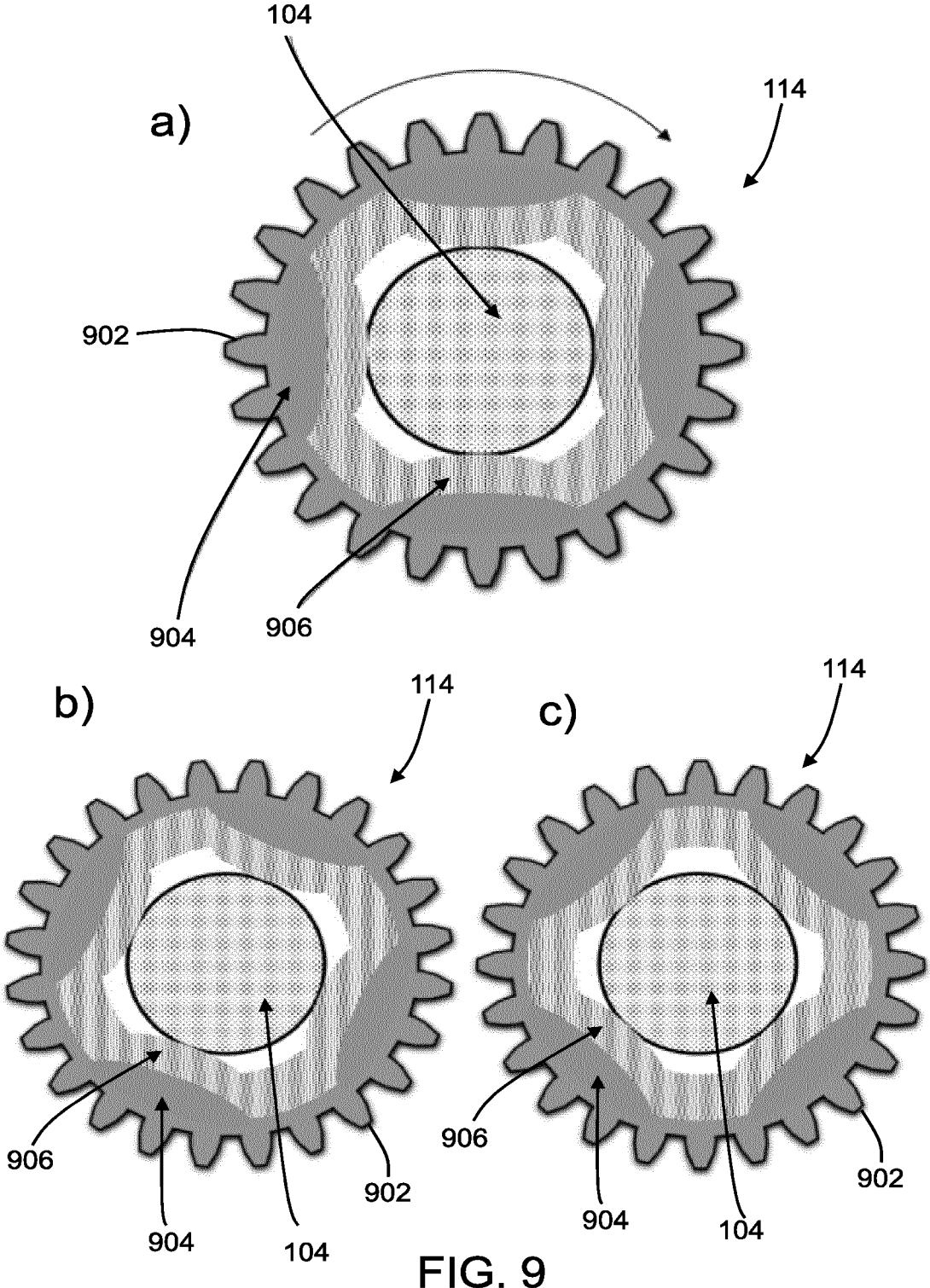
FIG. 9 shows a cross section of a rotating actuator device.

FIG. 9 shows a cross section of a rotating actuator device 114. In this example, a rotating mechanical element 902 with protrusions 904 is used that deform an elastic layer 906 in a cyclic manner, thereby applying a pressure at a sequence of locations for fixing the housing 102 (not shown) to a finger 104. The rotating actuator device 114 contains the rotating mechanical element 902, a motor inducing this rotation (not shown) and an elastic layer 906 that is in contact with the skin of the finger 104. The electronic circuit 202 is used to drive the motor for inducing rotations and the sensor. To prevent rotation of the housing 102 with respect to the finger 104, two counter rotating mechanical elements 902 can be driven by the same motor.

The cross section shown is of the position of one of the rotating mechanical elements 902. The rotating mechanical element 902 is illustrated with four protrusions 904 locally indenting the elastic layer 906 and thereby exerting a local pressure on the finger 104. The four protrusions 904 create a continuous fixing of the finger 104.

A motor, via a gearbox, controls the speed of rotation, typically in the order of one revolution per minute. FIG. 9*a* shows the actuator device 114 before any rotation (i.e. the actuator system is in a first state), FIG. 9*b* shows the actuator device 114 after rotating 22.5 degrees (i.e. the actuator system is in a second state) and FIG. 9*c* shows the actuator device 114 after rotating 45 degrees (i.e. the actuator system is in a third state).

Both the cross section of the actuator device 114 as well of the finger 104 are displayed in a schematic fashion.

After placing the housing 102 over the finger 104 and subsequently powering the electronic circuit 202 by, for example, connecting the device to a patient monitor, the rotation is started. The elastic layer 906 may have a certain roughness at the side of the finger 104 aiding the fixing of the finger 104. The continuous rotation causes the pressure to be alternately positioned at different locations of the finger 104. Due to the protrusions 904, the finger 104 is not pressurized over its complete circumference thereby minimizing blocking the blood flow in the finger 104. Such a rotating element 902 works in affiliation with a second rotating element that rotates in a counter direction with respect to the first one, thereby minimizing the net rotating force on the finger 104.

The elastic layer 906 between rotating element 902 and finger 104 may be fixed to the housing 102 (so not fixed on the rotating element 902). In this case there would be friction between rotating element 902 and the elastic layer 906. However, there would be no friction between elastic layer 906 and finger 104 due to rotation (only friction due to the pressure from the protrusions 904 on the finger 104).

Alternatively, the elastic layer 906 could be fixed to the rotating element 902 (i.e. not fixed to the housing 102). In this alternative case there would be no friction between rotating element 902 and the elastic layer 906. However, there would be friction between elastic layer 906 and finger 104. In this case, the elastic layer 906 would preferably be smooth to reduce rotation friction whilst maintaining sufficient fixing of the finger 104.

The number of protrusions 906 can again be less or more then the depicted four.

Figure 10:
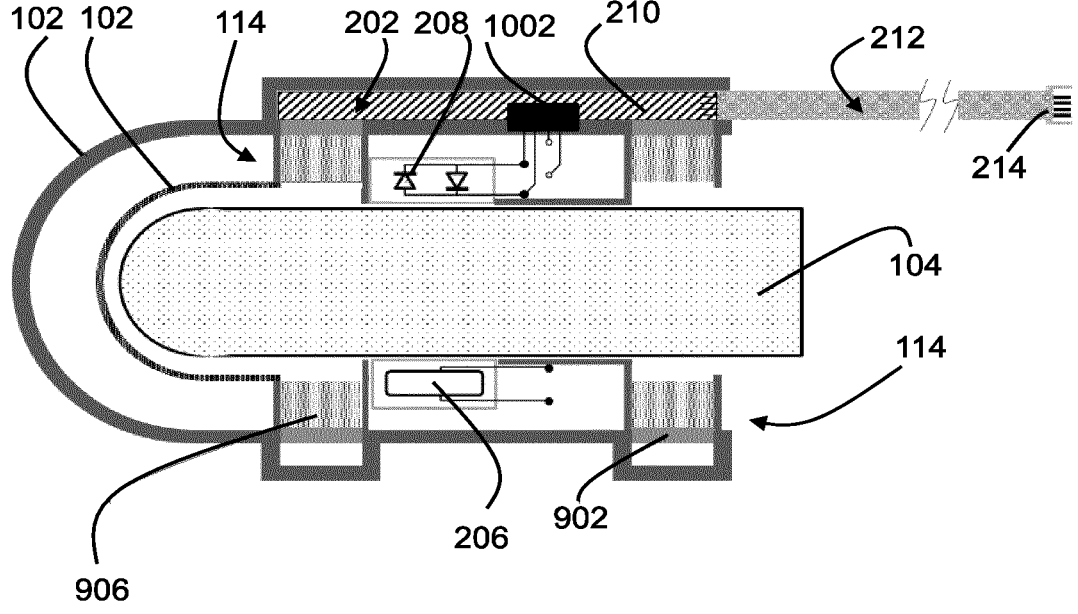
FIG. 10 shows a cross section along the length of the device with two rotating actuator devices.

FIG. 10 shows a cross section along the length of the device with two rotating actuator devices 114. The rotating elements 902 may rotate counter to each other. For reference, the LEDs 208, photodetector 206, housing 102, cable 212 and connector 214 are depicted. There are bearings between the rotating elements 902 and the housing 102 (not drawn). The motor and gearboxes 1002 are positioned on the PCB of the electronic circuit 202. One of the gearboxes 1002 provides a counter wise rotation to one of the rotating elements 902. Motors that generate a circular of linear motion leveraged to apply a pressure could be used.

Alternative actuator devices 114 include the use of electrical coils to exert a force on magnets that subsequently generate a pressure. Shape memory materials can also be used to generate pressure by changing its shape with an electrical heater.

The layer of material that is in direct contact with the skin of the finger 104 could be replaced by an annulus shaped pouch containing an absorber (i.e. a moisture trapping element). The pouch is made of a top sheet which has particular holes that function as a fluid diode. For the parts that are not pushed against the skin (i.e. there is no pressure between skin and pouch), the holes are open and allow sweat to be taken up by the pouch thereby keeping the skin dry. This contributes to the comfort of the subject wearing the device. For the parts that are pushed against the skin the holes are closed and prevent sweat from being squeezed back to the skin.

The previously mentioned examples are used on a finger 104. However, these examples could also be used on any body part 104 that can be clamped by exerting opposing pressures, such as the ear. However, there are body parts 104 where this is rather impractical. For instance, for reflective SpO2 sensors may be positioned on the forehead or on the torso. A band may be used around the head or torso to apply a pressure, however this would not contribute to a comfortable feeling and, on the torso, this results in a respiration cycle dependent pressure.

For such body locations (e.g. the forehead and the torso) an alternative pressure device is needed for local and temporal relief of pressure.

Figure 11:
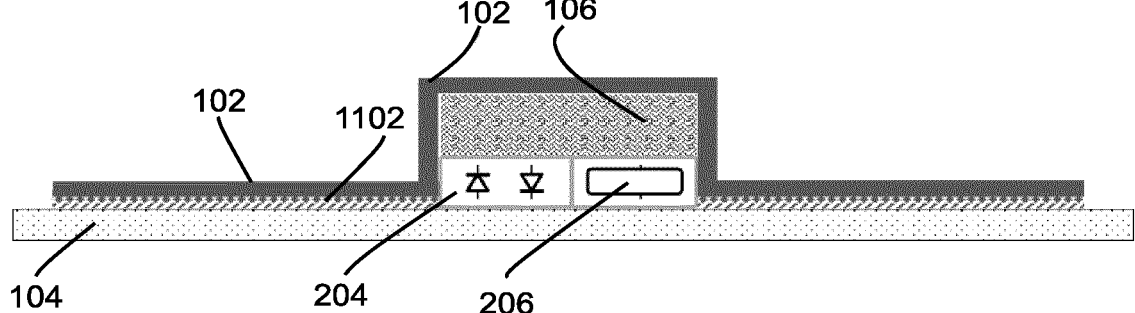
FIG. 11 shows a cross section of a device with a reflective SpO2 sensor.

FIG. 11 shows a cross section of a device with a reflective SpO2 sensor. Good contact between LED unit 204 and photodetector 206 of the SpO2 sensor and the skin is required for reliable SpO2 measurements. Appropriate contact can be given by pressure from an actuator element 106.

In FIG. 11, a cross section is shown of the device comprising a rigid housing 102 containing an SpO2 sensor (consisting out of two LEDs in an LED unit 204 and one photodetector 206 in sub housings). On top of the sub housings there is an actuator element 106 (such as an electro active polymer or an inflatable balloon). In this case, pressure is applied only when a measurement is taken by expanding the actuator element 106 (i.e. the actuator system is in a first state). Relief of the pressure is obtained by deactivation of the actuator element 106 (i.e. the actuator system is in a second state). Measurements can only be carried out when the pressure is applied (typically for several tens of seconds to several minutes) and then have a pressure relief period of several tens of seconds to several minutes. The area on which the housing 102 is attached, by an adhesive layer 1102, is larger than the area of the actuator element, thereby minimizing the force per surface area exerted on the body part 104 under the adhesive layer 1102.

The actuator system of the example shown in FIG. 11 only contains one actuator element 106 whereby pressure relief is obtained by activating and deactivating the actuator element 106 in a cyclic manner. However. The actuator system could comprise more than one actuator element 106 activating simultaneously, or activating one (or more) when the other(s) are deactivated. The actuator system could also comprise more than one actuator device comprising more than one set of actuator elements 106 as previously discussed.

For accurate SpO2 measurements, a suitable pressure between the body part 104 and sensor (LED unit 204 and photodetector 206) is required. This "optimal" pressure depends on many parameters and it varies from person to person. Active pressure optimization can significantly improve SpO2 measurement accuracy. For instance, for a measurement on the torso, different postures (supine or lying on the side) require different pressures to suppress artefacts in the PPG (photoplethysmography) signal obtained by the photodetector 206. A 3D accelerometer can be used to determine the posture and adjust the pressure of the actuator elements 106 accordingly.

PPG signal features may also be used to optimize the pressure. When the pressure is too low, artefacts due to venous and skin tissue pulsation are present on top of the arterial pulsation. When pressure increases, the artefacts become smaller and the accuracy increases for SpO2 measurements (from the PPG signal). However, at higher pressures, the arterial pulsation and perfusion start to decrease again, thus reducing the SpO2 measurement accuracy. Accelerometer measurements and/or PPG signal features may be used as input parameters for an algorithm that derives an optimal pressure and generates a feedback signal for pressure adjustment.

A feedback loop may also be created that controls the exerted pressure such that the amplitude of the cardiac component in the PPG signal is maximized. Maximizing the amplitude of the cardiac component in the PPG signal may result in uncomfortably high pressures, thus the feedback loop would have a maximum pressure limit which is not to be exceeded to assure comfort.

Furthermore, when the feedback loop identifies the external pressure at which the cardiac component in the PPG signal has maximum amplitude, this external pressure provides an indication of the mean arterial blood pressure at the body part 104. Thus, the feedback loop can simultaneously optimize the contact pressure and provide an estimate of the mean arterial pressure.

Estimates of venous oxygen saturation could also be obtained. For example, an estimate of venous oxygen saturation can be obtained when changing the set of actuator elements 106 fixing the SpO2 sensor. In the process of changing the fixing position, at one point in time both sets of actuator elements 106 are activated. At this time the externally applied pressure is fully circumferential and maximum, which reduces the venous return and thus leads to a decrease in the PPG signal baseline provided that the sensor fixing occurs proximal to the LEDs and photodiode. The ratio between the relative decrease in the baseline of the red and infrared PPG signals can provide an estimate of the venous oxygen saturation.

Furthermore, when one set of actuator elements 106 is deactivated again, this will lead to a subsequent increase in the venous return, resulting in an increase in the baseline of the PPG signals. The ratio between the relative increase in the baseline of the red and infrared PPG signals can provide a second estimate of the venous oxygen saturation. Both estimates can be combined into a single estimate of venous oxygen saturation or either of the two can be used to provide an estimate of the venous oxygen saturation. Both sets of actuator elements 106 need to be activated sufficiently long to achieve a sufficient decrease in the baseline of the PPG signal. The duration of simultaneous activation of both the sets of actuator elements 106 can be made adaptive, based on the decrease in baseline measured in the PPG signals.

The sets of actuator elements 106 can also be used to induce a low amplitude variation in the SpO2 sensor fixing pressure at a known frequency. The average pressure and pressure variation should be sufficiently small to only induce variations in venous blood volume and leave the arterial system unaffected. When extracting the variations in the red and infrared PPG signals that occur at this known frequency, it is possible to estimate the venous oxygen saturation analogous to how one would estimate arterial oxygen saturation. Variations in contact pressure to obtain an estimate of venous oxygen saturation can be induced intermittently, for example, following the moments when the fixing position is changed.

The controller 202 may be configured to perform the processing of the PPG signal, 3D accelerometer signal and others as mentioned in the above examples. Alternatively, a separate processor may be used to perform the processing as mentioned in the above examples. The processor could be connected (wired or wirelessly) to the controller 202 in order to give the controller 202 instructions on, for example, the pressure values, the time of switching etc. The controller 202 and/or processor could also be connected to a display for displaying any information previously discussed.

The above mentioned examples have been described using an SpO2 sensor. However, the device may also be designed with any other sensor which requires a fixing to a body part 104. For example, some heart rate sensors require at least some fixing to a body part 104 in order to measure the heart rate. Blood pressure measurements also typically require a pressure applied to a body part. Alternatively, the sensor could be for measuring the amount of carboxyhemo-globin and/or methemoglobin in addition, or as an alternative, to measurements of oxyhemoglobin (i.e. hemoglobin with bound oxygen).

The time between switching the actuator elements 106 (or sets of actuator elements 106) will depend on the subject, the body part 104, the amount of pressure applied, the number of actuator elements 106 activated etc. In general, the time between switching should not be less than one second and not be more than 20 minutes. In particular, the time between switching between a first state and a second state should ensure the sensor can perform the measurements adequately and that the subject does not experience unnecessary levels of discomfort.

The example above have only two (or three) states for the actuator system. The actuator system has at least two states to provide pressure relief. However, the actuator system could comprise any other number (larger than two) of states to provide even more localized (e.g. along the length of the housing 102) pressure relief.

The actuator system may comprise annular bands as long as the blood flow is not restricted too much. If blood flow is restricted around the circumference of the body part, even if the fixing is changed intermittently to another position, the blood flow could still be restricted. For example, a circular elastic band around a finger will restrict blood flow. If two such bands at different positions are utilized in an alternate fashion, the blood flow will still be restricted. Hence, the housing is preferably fixed to the body location using an actuator system that exerts a pressure over only a portion of the circumference of the finger or other body location as explained above.

Preferably, the electrical connection port used by the device is the same, or similar, to ports used by current sensors (e.g. a four pin connection port). Thus, the invention can be used with currently existing patient monitors. The sensor may then operate with the same functionality as offered by the current ports of patient monitors, using two pins to drive the alternate fixing. Internal software of the patient monitor may be updated to enable use of the new device, while retaining compatibility with existing sensor types.

As discussed above, embodiments make use of a controller 202. The controller 202 can be implemented in numerous ways, with software and/or hardware, to perform the various functions required. A processor is one example of a controller which employs one or more microprocessors that may be programmed using software (e.g., microcode) to perform the required functions. A controller 202 may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller 202 may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller 202 or may be transportable, such that the one or more programs stored thereon can be loaded into a processor or controller.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

The mere fact that certain measures are recited in mutually different dependent claims does not indicate that a combination of these measures cannot be used to advantage.

If the term "adapted to" is used in the claims or description, it is noted the term "adapted to" is intended to be equivalent to the term "configured to".

Any reference signs in the claims should not be construed as limiting the scope.

The invention claimed is:

1. A device for measuring a body parameter for a subject while fixing itself to a body part of the subject, the device comprising:

a sensor for measuring the body parameter;

a housing element for positioning the sensor on the body part of the subject;

an actuator system within the housing element for fixing the device to the body part of the subject by applying a pressure to a body location of the body part for fixing the housing, wherein the actuator system comprises two states:

a first state based on the actuator system applying a first pressure to a first area of the body part; and a second state based on the actuator system applying a second pressure to a second area of the body part different to the first area, such that the first area has a relief from the first pressure while the second pressure is applied to the second area; and a controller configured to apply the first and second states at different times such that applied pressure is alternately positioned at said different areas of the body part.

2. The device of claim 1, wherein the actuator system comprises at least two actuator elements, each actuator element being configured to change in volume or shape when the actuator element is stimulated, and wherein the controller is further configured to stimulate the actuator elements to define the state of the actuator system.

3. The device of claim 2, wherein the actuator elements are based on electro active polymers configured to expand in volume when a voltage is applied and wherein the controller is further configured to apply a voltage to the electro active polymers.

4. The device of claim 2, wherein the actuator elements are inflatable elements configured to expand when they are inflated.

5. The device of claim 4, further comprising a pump for inflating the inflatable elements and wherein the controller is further configured to actuate the pump.

6. The device of claim 1, wherein the controller is further configured to change the pressure applied to the body part of the subject by the actuator system.

7. The device of claim 6, further comprising an accelerometer for determining the position of the subject and wherein the controller is further configured to change the pressure applied to the body part of the subject by the actuator system based on the position of the subject.

8. The device of claim 1, wherein the sensor is a pulse oximeter which comprises an LED unit and a photodetector, wherein the photodetector is configured to obtain a signal relating to the saturation percentage of oxygen in blood.

9. The device of claim 8, wherein the LED unit is placed at the extremity of a first actuator element and the photodetector is placed at the extremity of a second actuator element.

10. The device of claim 8, wherein the controller is further configured to control the actuator system to apply a predetermined pressure to the body part, wherein the application of the pre-determined pressure to the body part reduces the venous contribution to the signal obtained by the photodetector.

11. The device of claim 1, further comprising an adhesive layer at the interface between the housing element and the body part of the subject and wherein the actuator system is configured to apply a pressure between the sensor and the body part.

12. The device of claim 1, wherein the actuator system comprises:
a rotating element with two or more protrusions, wherein the controller is configured to rotate the rotating element when changing states; and
an elastic layer between the rotating element and the body part of the subject.

13. The device of claim 1, further comprising a friction enhancing layer at the interface between the device and the body part of the subject.

14. The device of claim 1, further comprising a moisture trapping element at the interface between the device with the body part of the subject for reducing moisture build up at said interface.

15. A method for measuring a body parameter for a subject with a device comprising a sensor, the method comprising:
applying a first pressure to a first area of a body part using an actuator system, wherein the actuator system is within a housing element of the device and wherein the housing element is fixed thereby to the body part;
applying a second pressure to a second area of the body part, different to the first area of the body part such that the first area has a relief from the pressure while the second pressure is applied to the second area, using the actuator system at a different time to the first pressure being applied to the first area of the body part such that applied pressure is alternately positioned at said different areas of the body part; and
measuring the body parameter with a sensor which is positioned on the body part by the housing element.

* * * * *